US00PP11004P

United States Patent [19]

Doguet

[11] Patent Number: Plant 11,004

[45] Date of Patent: Jul. 13, 1999

[54] 'DDBGI' BUFFALOGRASS

[75] Inventor: David L. Doguet, Austin, Tex.

[73] Assignee: C & D Turfgrass, Ltd., Bastrop, Tex.

[21] Appl. No.: 08/633,391

[22] Filed: Apr. 16, 1996

Related U.S. Application Data

[63] Continuation of application No. 08/633,961, Apr. 15, 1996., abandoned

[51] Int. Cl.[6] ..... A01H 5/00

[52] U.S. Cl. ..... Plt./391

[58] Field of Search ..... Plt./90

[56] References Cited

U.S. PATENT DOCUMENTS

| | | | |
|---|---|---|---|
| P.P. 7,539 | 5/1991 | Engelke et al. | Plt./391 |
| P.P. 8,475 | 11/1993 | Riordan et al. | Plt./391 |
| P.P. 9,208 | 7/1995 | Mancino | Plt./391 |

*Primary Examiner*—James R. Feyrer
*Attorney, Agent, or Firm*—Suiter & Associates PC

[57] ABSTRACT

A vegetatively reproduced buffalograss cultivar, named 'DDBGI', is distinguished by its low growth habit, medium light green color, high density, excellent vigor, heat and drought tolerance, adaptation in the South, and low maintenance requirements.

3 Drawing Sheets

CROSS REFERENCE TO RELATED APPLICATION

This application is a continuation of plant application Ser. No. 08/633,961, filed Apr. 15, 1996, now abandoned.

BACKGROUND

Buffalograss, *Buchloë dactyloides* (Nutt) Engelm., is a perennial, low-growing, drought tolerant species that spreads by profusely branching stolons and thrives under semi-arid conditions even under heavy grazing pressure. Buffalograss is the only turfgrass species which can withstand all combinations of cold, heat and drought stress and still maintain an attractive turf under low to medium maintenance levels.

Native to an area extending from Central Mexico to Southern Canada which receives an annual precipitation of 38 to 63 cm, Buffalograss has a secondary range of adaptation along the perimeter of its primary range, in which it can displace less well-adapted grasses given favorable conditions of soil, altitude (<2000m) and competition. Buffalograss cannot endure competition of taller species under climatic conditions that favor these species.

Following the drought of the 1930's, buffalograss reestablished itself as a grass of great agricultural and conservation importance, having survived the combined effects of dust, drought, plowing and overgrazing. Its aggressive stoloniferous growth habit and dense sod forming capabilities proved very effective at binding soil to prevent wind and water erosion. Buffalograss sod also exhibits high water holding capacities, usually 57 to 60%.

Buffalograss has emerged as an excellent drought-resistant native species with an evapotranspiration rate of less than 6 mm per day, less than any other commonly used warm or cool season turfgrass. Some of the characteristics responsible for this drought resistance are its finely branched root system, aggressive low growing aerial parts and the ability of leaf blades to limit transpiration by tightly rolling during drought stress. Buffalograss is able to go dormant sooner than other grasses and revives quickly when the drought stress is removed. In comparison with other grasses, at reduced mowing heights buffalograss shows increased survival, growth rate and weed resistance. These characteristics all make buffalograss a potentially outstanding turfgrass with minimal negative effects on the environment.

Buffalograss can be established by two methods: vegetative propagation or seeding. Traditionally, vegetative propagation of plugs or sod pieces has been employed because of difficulties in seed production and seed establishment. Recent developments in equipment such as automated pluggers and "big roll" sod handlers have further enhanced the appeal of vegetative propagation. Improvements have also been made in seed production and seed treatment.

Buffalograss use is increasing, especially in low maintenance areas. It has been successfully established on highway shoulders and right-of-ways, airfield runways, cemeteries, parks, golf courses and other athletic field areas. Because of environmental concerns, water shortages and changes in personal priorities, buffalograss now has tremendous potential as a turfgrass. Efforts in breeding and development of buffalograss are relatively new, and the emphasis of this work has been on developing turf-type cultivars which maintain the ecological efficiency of the species, yet have a lower growth habit, increased rate of spread, improved color, extended growing season, increased density, and good recuperative potential.

SUMMARY OF THE INVENTION

'DDBGI' buffalograss is distinguished from other commercially available cultivars in being a vegetatively propagated female plant with a more dwarf growth habit than 'Prairie', '609', '315' or '378' buffalograsses. 'DDBGI' has less pubescence than '315' or '378', and it has a narrower and shorter leaf than other cultivars. 'DDBGI' has a late Spring greenup, a fine leaf texture, a high percent density and excellent quality when grown in the South, its area of adaptation. In the North, 'DDBGI' shows more winter damage (% cover) than other commercially available cultivars, often resulting in reduced turfgrass quality ratings and performance during the second year of establishment.

BRIEF DESCRIPTION OF THE PHOTOGRAPHS

DETAILED DESCRIPTION OF THE PLANT

Figure 1:
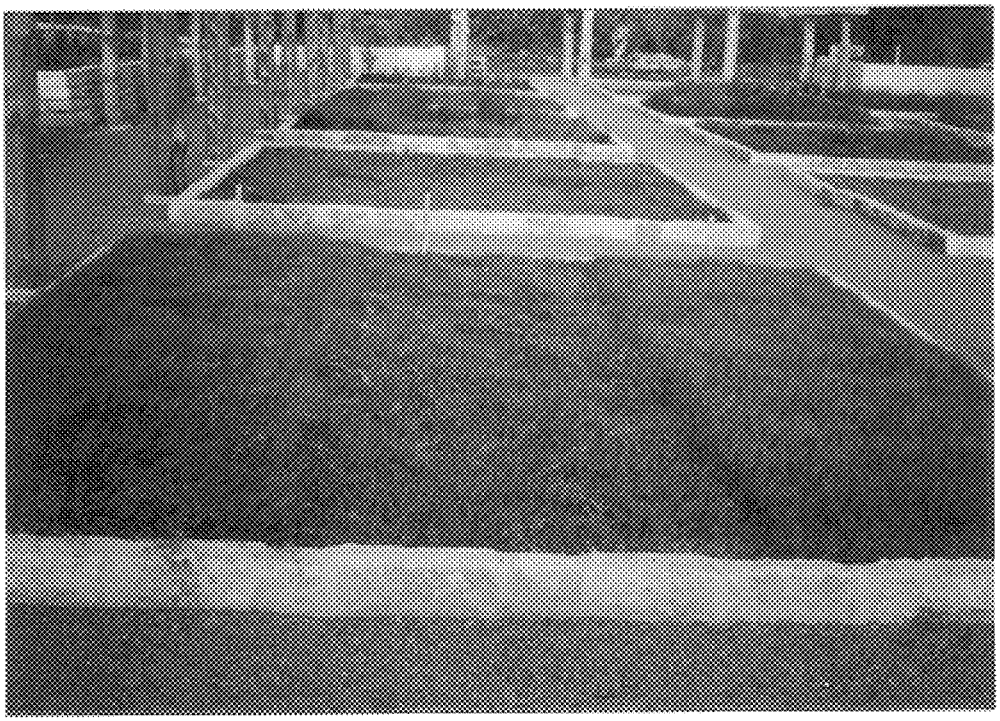
FIG. 1 is a photograph of 'Prairie' (left), 'DDBGI' (center) and '609' (right) buffalograss at the National Wildflower Institute, Austin, Tex.
Figure 2:
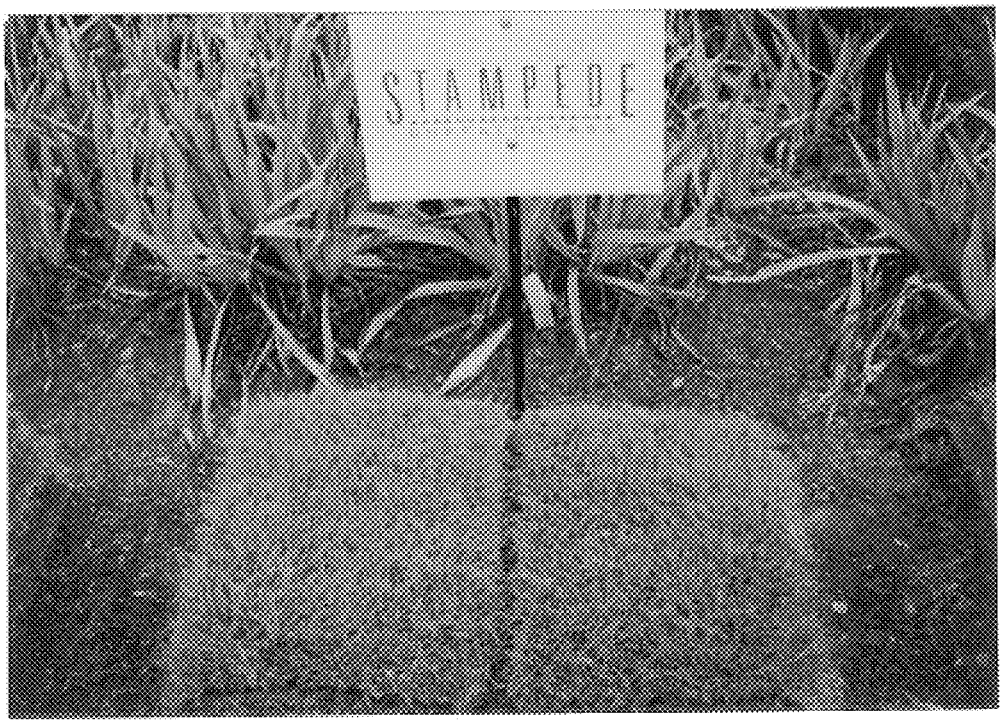
FIG. 2 is a photograph of 'DDBGI' ('Stampede') buffalograss sod, Austin, Tex.
Figure 3:
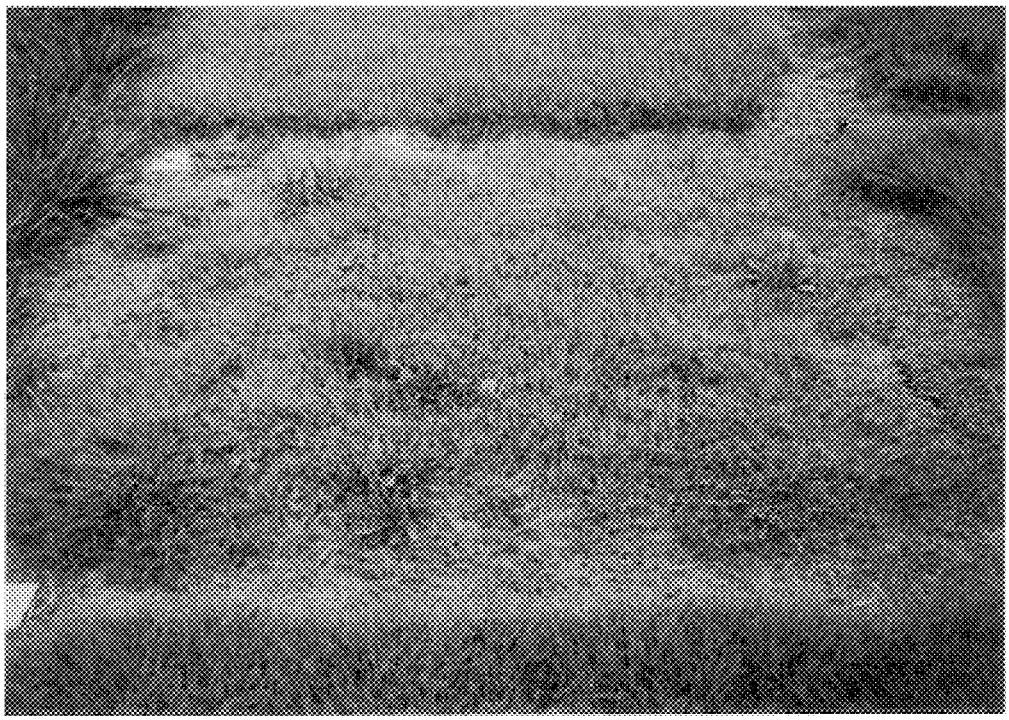
FIG. 3 is a photograph of a 'DDBGI' buffalograss at ARDC, Mead, Nebr.
Figure 4:
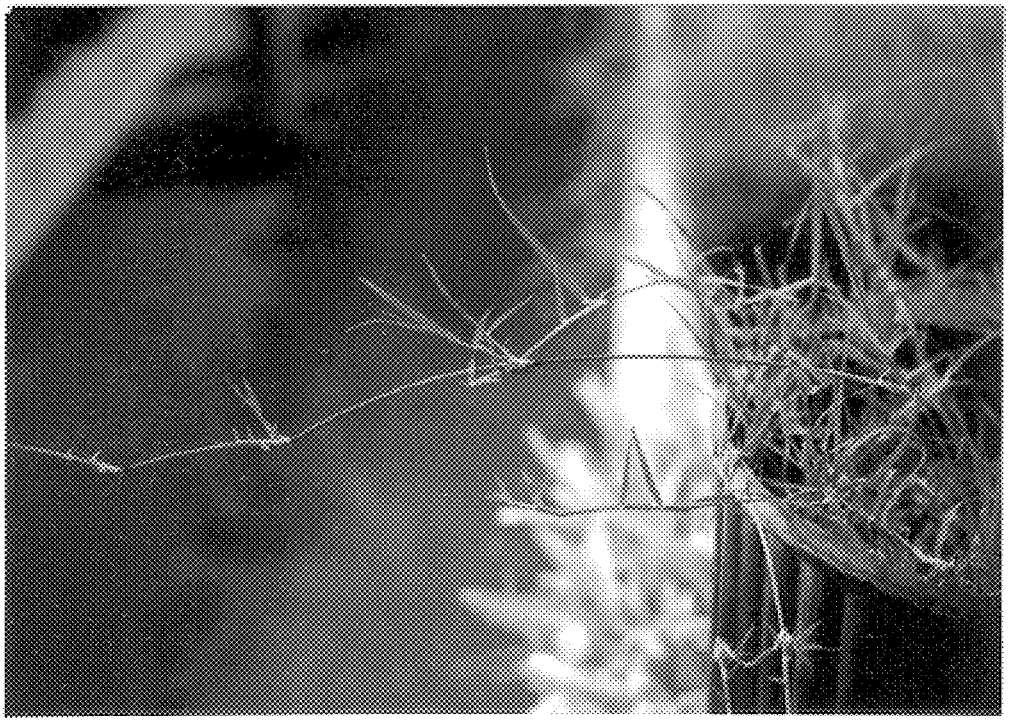
FIG. 4 is a photograph of 'DDBGI' buffalograss stolon in greenhouse, Lincoln, Nebr.
Figure 5:
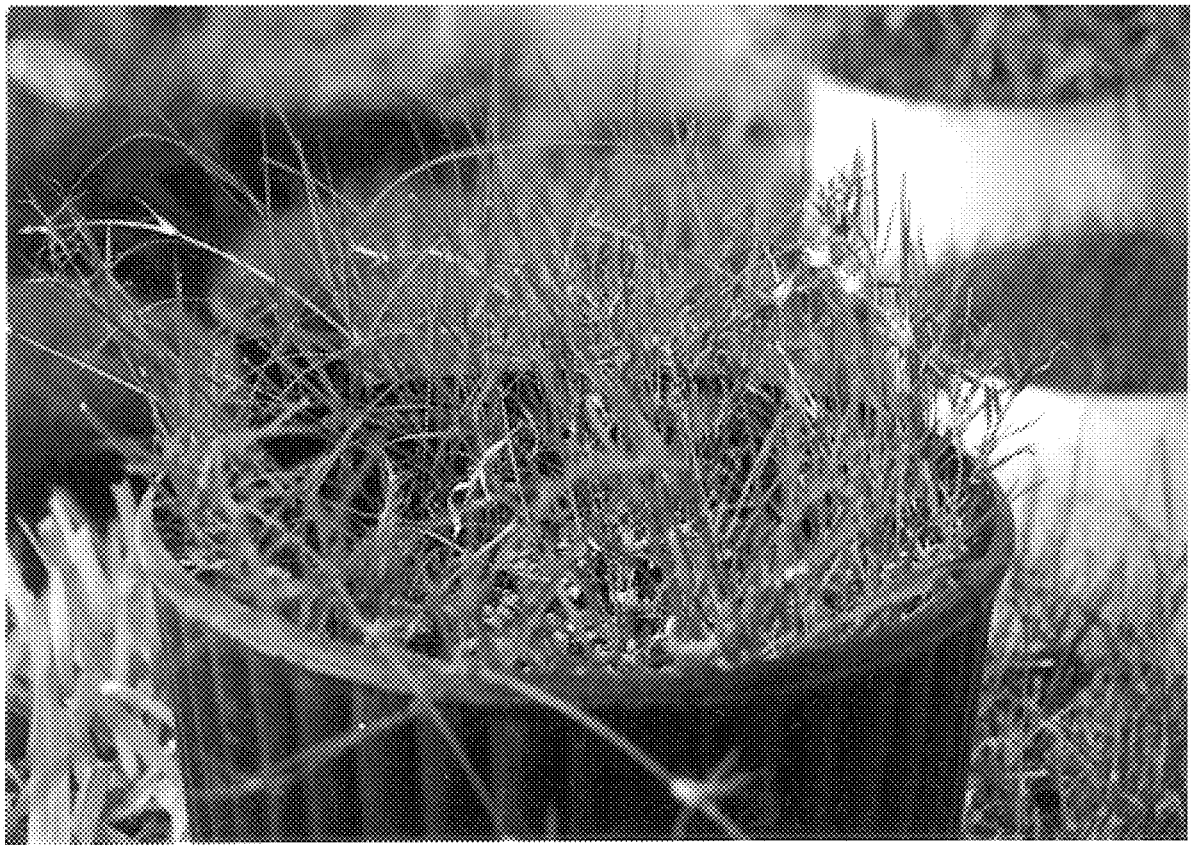
FIG. 5 is a photograph of 'DDBGI' buffalograss in greenhouse, Lincoln, Nebr.

'DDBGI', is a female plant collected in 1985 on the Texas Gulf Coast from an old stand of buffalograss growing on a golf course. It was then asexually propagated and maintained for approximately one year in the applicant's private nursery in Austin, Tex. where it was selected for further cultivation due to its dwarf habit and rapid growth. 'DDBGI' was then vegetatively planted and maintained in a breeder's nursery in Bastrop, Tex.

During formal plant trials 'DDBGI' was labeled 'Stampede', a prototypic trade name for which application for trademark protection was filed on May 26, 1995 in anticipation of marketing by the owners of 'DDGBI', C & D Turfgrass, Ltd. The trademark application number is 74-680,180. Hence, 'DDGBI' is represented as 'Stampede' in the plant trial tables and in some photographs from that era though the grass was not placed in commerce until late 1995. 'DDBGI' was initially evaluated in 1993 at the J.S. Anderson Turfgrass Research Facility along with hundreds of other selections in replicated turfgrass trials. 'DDBGI' has also been evaluated at Georgia Agricultural Research and Extension Center at Griffin, Ga. In most tests 'DDBGI' was compared to 'Texoka' (a commercial standard), 'Prairie' (a release from Texas A & M), '609', '378' and '315' (releases from the University of Nebraska) and many other experimentals.

Under certain, incompletely characterized environmental or climatic conditions, such as unusually cold temperatures, 'DDBGI' may produce some male inflorescences on the female plant. Although viable pollen may be shed, this along with production of viable seed can be controlled by regular mowing. As with other contaminations of monoculture, roguing can be used to maintain purity.

The growth characteristics of buffalograss can be used to distinguish one cultivar from others. The internode lengths of 'DDBGI' are less than that of 'Texoka', 'Prairie' and '609', but similar to '378' (Table 1). The internode and node widths are comparable to all other genotypes (Table 1). The leaf blade length of 'DDBGI' is shorter than other genotypes, but only significantly shorter than '609' and 'Texoka'. Leaf width is less than 'Texoka', but comparable to the others (Table 2). 'DDBGI' has less leaf and node pubescence than '315', '378', and 'Texoka' (Table 3).

Buffalograss is a warm season species that will greenup later and go dormant earlier than cool season species such as Kentucky bluegrass. Although this may be a negative characteristic in the Northern part of the United States, buffalograss may have a longer growing season than other warm season turfgrasses in the South. Spring greenup has been evaluated at both the University of Nebraska and the University of Georgia. 'DDBGI' had a spring greenup rate slower than '315', '378' and 'Texoka', and comparable to '609' and 'Prairie' in Nebraska (Table 4). In Georgia, 'DDBGI' had faster greenup than '609' (Table 5). Fall dormancy ratings indicate that 'DDBGI' goes dormant at the same time as '609' and 'Prairie', but later than '315', '378' and 'Texoka' (Tables 6, 12). A buffalograss with later fall dormancy in the North would be advantageous. However, it is possible that this would cause a loss in winter hardiness.

Turfgrass quality is a rating used to indicate the aesthetic value of a turf cultivar. This characteristic is very important in buffalograss because its turf potential has been overlooked in the past. 'DDBGI' had average turfgrass quality in Georgia throughout the year (Table 7). At the University of Nebraska, 'DDBGI' had turfgrass quality ratings comparable to '315', '378', and 'Texoka' during its first year (Table 8). In the second year 'DDBGI' showed very poor quality (Table 9) because of winter damage.

'DDBGI' has a moderate rate of establishment. In Nebraska, 'DDBGI' had slower establishment than 'Texoka', and similar establishment to all the others during the first Summer (Table 10). Data taken a year after establishment show 'DDBGI' has poor cover and quality after one Winter (Table 6). This is a good indicator that 'DDBGI' is not well adapted to the cold winters of the North.

Turfgrass color is an important component of turfgrass quality. In Nebraska, 'DDBGI' had an attractive, medium green color comparable to '315', 'Prairie' and 'Texoka' throughout the growing season (Table 11).

The Variety

Origin: Cultivar of a single superior female plant collected in the Gulf Coast of Texas.

Classification:

*Botanic.*—*Buchloë dactyloides* (Nutt.) Engelm.

Chromosome number: 40 chromosomes (tetraploid).

Form: Monocot Gramineae.

Growth habit: A perennial female plant with a stoloniferous growth habit allowing vegetative propagation. It is able to spread under non-competitive conditions otherwise favorable for stolon production. It has a very fibrous root system which can have a depth of 100 to 150 cm. It will produce a dense, fine textured turf with excellent medium green color throughout most of the growing season.

Establishment rate:

*Plugs.*—10 to 14 weeks with irrigation.

*Sod.*—1 to 2 weeks.

*Sprigs.*—Not recommended.

Regions of adaptation: North/South from the Kansas-Oklahoma border to the Mexican border and East/West from Missouri to California. The full extent of 'DDBGI' geographic region of adaption is currently under investigation and may actually be wider.

Blade:

*Shape.*—Short, slender.

*Length* (*mature*).—Approximately 12 cm.

*Width.*—Approximately 1 mm.

*Pubescence.*—Less when compared to other buffalograsses.

Mature plant height: 15 cm.

Above canopy stolon production: minimal compared to 'Prairie'.

Internode length: 4 cm.

Internode width: 0.9 mm.

Node pigmentation: Green; anthocyanin may be noted at times.

Stolon color:

*Midsummer.*—Typically yellow green (137D*).

*Winter.*—Tan (161D*).

Leaf color:

*Midsummer.*—Medium green to green (137C*).

*Winter.*—Tan (161D*).

Soil adaptation:

*Heavy soils.*—Silty clay loam preferred, slightly acid to alkaline pH.

Female inflorescence: Present, heavy at certain portions of the growing season.

Male inflorescence: Under certain environmental conditions, 'DDBGI' may produce a few male inflorencences.

*Royal Horticultural Society Colour Chart Designations.

Comparative Data

The following tables provide data comparisons of selected characteristics of 'DDBGI' ('Stampede') compared to '609', 'Texoka', '315', '378' and 'Prairie'.

TABLE 1

Node and Internode Characteristics:
1993 University of Nebraska Greenhouse - Lincoln, NE

| | Internode 2(mm) | Internode 3 | Node width | Internode width |
|---|---|---|---|---|
| 'DDBGI' (Stampede) | 39.6 | 41.5 | 3.6 | 0.9 |
| 315 | 29.5 | 36.4 | 3.8 | |
| 378 | 44.9 | 45.3 | 3.8 | 0.9 |
| 609 | 56.8 | 63.5 | 4.3 | 1.0 |
| Prairie | 57.4 | 67.1 | 4.2 | 1.0 |
| Texoka | 54.1 | 57.7 | 3.3 | 0.9 |
| LSD (.05) | 10.2 | 12.1 | 0.6 | 0.1 |

TABLE 2

Leaf Characteristics:
1993 University of Nebraska Greenhouse - Lincoln, NE

| | Width (mm) | Length |
|---|---|---|
| 'DDBGI' (Stampede) | 1.0 | 121.3 |
| 315 | 1.1 | 137.3 |
| 378 | 1.1 | 158.4 |
| 609 | 1.2 | 163.5 |
| Prairie | 1.1 | 143.3 |
| Texoka | 1.6 | 224.0 |
| LSD (.05) | 0.2 | 40.3 |

TABLE 3

Pubescence[1]:
1993 University of Nebraska Greenhouse - Lincoln, NE

| | Node | Leaf | Collar |
|---|---|---|---|
| 'DDBGI' (Stampede) | 1.0 | 1.0 | 2.2 |
| 315 | 2.8 | 5.8 | 5.1 |
| 378 | 3.7 | 7.1 | 7.0 |
| 609 | 1.0 | 1.0 | 2.2 |
| Prairie | 1.0 | 1.3 | 3.7 |
| Texoka | 1.6 | 6.7 | 6.6 |
| LSD (.05) | 0.5 | 0.5 | 0.7 |

TABLE 4

Greenup:
1994 Buffalograss Evaluation - Mead, NE (Est. June 23, 1993)

| | Spring Greenup[1] 5/6 | Male Flowers[2] 6/24 | Uniformity[3] 8/19 |
|---|---|---|---|
| 'DDBGI' (Stampede) | 1.0 | 1.0 | 1.7 |
| 315 | 6.3 | 1.3 | 6.0 |
| 378 | 6.3 | 1.7 | 4.7 |
| 609 | 1.0 | 1.0 | 3.3 |
| Prairie | 1.0 | 1.7 | 4.3 |
| Texoka | 3.0 | 4.7 | 4.3 |
| LSD (.05) | 1.2 | 1.2 | 1.8 |

[1]Spring greenup is rated 1–9 with 9 = complete greenup.
[2]Male flowers is rated 1–9 with 1 = none.
[3]Uniformity is rated 1–9 with 9 = most uniform.

TABLE 5

Spring Greenup, Color and Leaf Texture:
1994 Buffalograss Evaluation - Griffin GA (Est. 1993)

| | Spring Greenup[1] | | |
|---|---|---|---|
| Cultivar | 3/21 | 3/31 | Spring Greenup Average |
| 'DDBGI' (Stampede) | 4.3 | 4.7 | 4.5 |
| 118 | 2.3 | 4.7 | 3.5 |
| 114 | 2.3 | 4.3 | 3.3 |
| 409 | 4.3 | 5.0 | 4.7 |
| 609 | 3.0 | 4.0 | 3.5 |
| 102 | 3.3 | 5.0 | 4.2 |
| 116 | 2.3 | 5.0 | 3.7 |
| LSD (.05) | 0.8 | 0.7 | 0.6 |

| | Color[2] | | | | Color | Leaf[3] |
|---|---|---|---|---|---|---|
| Cultivar | April | May | Sept | Oct | Average | Texture |
| 'DDBGI' (Stampede) | 2.0 | 4.7 | 4.3 | 3.3 | 3.6 | 6.3 |
| 118 | 2.3 | 5.0 | 4.7 | 4.0 | 4.0 | 5.7 |
| 114 | 2.0 | 4.0 | 3.3 | 3.0 | 3.1 | 5.0 |
| 409 | 2.3 | 5.0 | 4.7 | 4.0 | 4.0 | 5.7 |
| 609 | 2.0 | 4.7 | 4.3 | 4.0 | 3.8 | 5.7 |
| 102 | 2.0 | 4.0 | 3.3 | 3.3 | 3.2 | 5.0 |
| 116 | 2.0 | 4.0 | 3.0 | 3.7 | 3.2 | 5.3 |
| LSD (.05) | 0.5 | 1.0 | 0.9 | 1.1 | 0.4 | 0.7 |

[1]Greenup is rated 1–9 with 9 = complete green.
[2]Color is rated 1–9 with 9 = darkest green.
[3]Leaf texture is rated 1–9 with 9 = finest texture.

TABLE 6

Fall Dormancy:
1994 Buffalograss Evaluation - Mead, NE (Est. June 23, 1993)

| | % Cover | Fall Dormancy[1] | | |
|---|---|---|---|---|
| | 6/24 | 10/7 | 10/20 | Ave |
| 'DDBGI' (Stampede) | 1.7 | 8.7 | 7.7 | 8.2 |
| 315 | 94.3 | 4.7 | 2.7 | 3.7 |
| 378 | 85.0 | 4.3 | 3.0 | 3.7 |
| 609 | 26.3 | 8.7 | 7.7 | 8.2 |
| Prairie | 50.3 | 8.0 | 7.0 | 7.5 |
| Texoka | 96.0 | 7.0 | 4.7 | 5.8 |
| LSD (.05) | 18.1 | 1.2 | 1.0 | 1.0 |

[1]Fall dormancy is rated 1–9 with 9 = no dormancy.

TABLE 7

% Density and Quality:
1994 Buffalograss Evaluation - Griffin, GA (Est. 1993)

| | % Density | Quality[1] | | | |
|---|---|---|---|---|---|
| Cultivar | Fall | April | May | June | July |
| 'DDBGI' (Stampede) | 96.0 | 2.3 | 5.3 | 5.7 | 5.3 |
| 118 | 96.0 | 2.7 | 5.7 | 6.0 | 6.0 |
| 114 | 99.0 | 3.0 | 6.0 | 6.0 | 6.0 |
| 409 | 97.7 | 3.7 | 6.0 | 5.0 | 5.7 |
| 609 | 99.0 | 3.0 | 6.0 | 5.7 | 6.0 |
| 102 | 99.0 | 3.3 | 5.0 | 6.0 | 5.7 |
| 116 | 97.7 | 3.0 | 5.0 | 5.7 | 6.0 |
| LSD (.05) | 5.4 | 0.6 | 0.9 | 0.7 | 0.7 |

| | % Density | Quality[1] | | | Quality |
|---|---|---|---|---|---|
| Cultivar | Fall | Aug | Sept | Oct | Average |
| 'DDBGI' (Stampede) | 96.0 | 3.0 | 5.0 | 5.0 | 4.5 |
| 118 | 96.0 | 4.0 | 5.3 | 5.0 | 5.0 |
| 114 | 99.0 | 4.0 | 4.3 | 5.0 | 4.9 |
| 409 | 97.7 | 3.3 | 5.3 | 5.0 | 4.9 |
| 609 | 99.0 | 3.3 | 5.0 | 5.0 | 4.9 |
| 102 | 99.0 | 3.7 | 4.0 | 5.0 | 4.7 |
| 116 | 97.7 | 3.7 | 3.7 | 5.0 | 4.6 |
| LSD (.05) | 5.4 | 0.8 | 0.8 | 0.0 | 0.3 |

[1]Quality is rated 1–9 with 9 = best quality.

TABLE 8

Turfgrass Quality[1]:
1993 Buffalograss Evaluation - Mead, NE (Est. June 22, 1993)

| | 8/12 | 9/29 | Ave. |
|---|---|---|---|
| 'DDBGI' (Stampede) | 5.3 | 6.7 | 6.0 |
| 315 | 5.3 | 6.7 | 6.0 |
| 378 | 4.5 | 5.0 | 4.8 |
| 609 | 5.7 | 6.3 | 6.0 |
| Prairie | 3.3 | 5.7 | 4.5 |
| Texoka | 6.0 | 5.0 | 5.5 |
| LSD (.05) | 1.5 | 1.2 | 1.1 |

[1]Turfgrass quality is rated 1–9 with 9 = best.

TABLE 9

Turfgrass Quality:
1994 Buffalograss Evaluation - Mead, NE (Est. June 23, 1993)

| | 6/22 | 7/19 | 8/18 | 9/27 | Ave |
|---|---|---|---|---|---|
| 'DDBGI' (Stampede) | 1.0 | 2.3 | 2.0 | 2.0 | 1.8 |
| 315 | 8.0 | 7.3 | 6.0 | 5.3 | 6.7 |
| 378 | 4.3 | 5.0 | 5.0 | 3.7 | 4.5 |
| 609 | 2.0 | 3.7 | 3.3 | 5.3 | 3.6 |
| Prairie | 2.3 | 3.7 | 4.7 | 5.0 | 3.9 |
| Texoka | 5.0 | 4.3 | 5.7 | 5.3 | 5.1 |
| LSD (.05) | 1.4 | 1.1 | 1.2 | 1.3 | 0.9 |

[1]Turfgrass quality is rated 1–9 with 9 = best.

TABLE 10

Percent Turfgrass Cover:
1993 Buffalograss Evaluation - Mead, NE (Est. 1993)

| | 7/28 | 6/17 | 9/29 | Ave |
|---|---|---|---|---|
| 'DDBGI' (Stampede) | 15.0 | 26.7 | 90.0 | 43.9 |
| 315 | 15.0 | 30.0 | 90.0 | 45.0 |
| 378 | 10.0 | 23.8 | 72.5 | 35.4 |
| 609 | 16.7 | 35.0 | 90.0 | 47.2 |
| Prairie | 25.0 | 08.3 | 93.3 | 42.2 |
| Texoka | 28.3 | 60.0 | 93.3 | 60.6 |
| LSD (.05) | 20.4 | 10.7 | 13.6 | 12.5 |

TABLE 11

Color:
1994 Buffalograss Evaluation - Mead, NE (Est. June 23, 1993)

| | 7/7 | 7/19 | Ave |
|---|---|---|---|
| 'DDBGI' (Stampede) | 5.0 | 5.0 | 5.0 |
| 315 | 6.3 | 5.3 | 5.8 |
| 378 | 6.7 | 6.3 | 6.5 |
| 609 | 7.0 | 5.7 | 6.3 |
| Prairie | 5.7 | 5.0 | 5.3 |
| Texoka | 5.3 | 5.0 | 5.2 |
| LSD (.05) | 1.6 | 1.0 | 1.0 |

[1]Turfgrass color is rated 1–9 with 9 = darkest green.

TABLE 12

Color and Fall Dormancy:
1993 Buffalograss Evaluation - Mead, NE (Est. June 22, 1993)

| | Color[1] | Dormancy[2] | | |
|---|---|---|---|---|
| | 9/29 | 9/29 | 10/14 | Ave |
| 'DDBGI' (Stampede) | 5.3 | 7.7 | 8.0 | 7.8 |
| 315 | 5.7 | 6.0 | 4.7 | 5.3 |
| 378 | 5.5 | 6.0 | 3.8 | 4.9 |
| 609 | 6.0 | 9.0 | 8.3 | 8.7 |
| Prairie | 5.0 | 7.7 | 8.0 | 7.8 |
| Texoka | 5.7 | 6.0 | 4.3 | 5.2 |
| LSD (.05) | 0.8 | 0.8 | 1.1 | 0.7 |

[1]Turfgrass color is rated 1–9 with 9 = best.
[2]Turfgrass dormancy is rated 1–9 with 9 = no dormancy.

I claim:

1. A new and distinct perennial female buffalograss plant substantially distinguished by its low growth habit, medium light green color, high density, excellent vigor, heat and drought tolerance, adaptation to the South, and low maintenance requirements as herein shown and described.

* * * * *

UNITED STATES PATENT AND TRADEMARK OFFICE

CERTIFICATE OF CORRECTION

PATENT NO. : Plant 11,004

DATED : July 13, 1999

INVENTOR(S) : David L. Doguet

It is certified that error appears in the above-indentified patent and that said Letters Patent is hereby corrected as shown below:

Column 5, after the last line therefore, insert

-- [1]Pubescence is rated 1-9 with 1= no pubescence and 9= heavy pubescence.--.

Column 7, line 41, Table 9, in the table heading thereof, "Turfgrass Quality:" should read -- Turfgrass Quality[1]: --

Column 8, line 14, Table 11, in the table heading thereof, "Color:" should read -- Color[1]: --

Signed and Sealed this

Sixth Day of February, 2001

*Attest:*

*Attesting Officer*

Q. TODD DICKINSON

*Director of Patents and Trademarks*